United States Patent [19]

Schinzel et al.

[11] Patent Number: 4,791,205
[45] Date of Patent: Dec. 13, 1988

[54] BISBENZOXAZOLYLNAPHTHALENES CONTAINING SULFONATE OR SULFONAMIDE GROUPS, A PROCESS FOR THEIR PREPARATION AND THEIR USE

[75] Inventors: Erich Schinzel; Hans Frischkorn, both of Hofheim am Taunus; Thomas Martini, Kelkheim (Taunus), all of Fed. Rep. of Germany

[73] Assignee: Hoechst Aktiengesellschaft, Frankfurt am Main, Fed. Rep. of Germany

[21] Appl. No.: 52,783

[22] Filed: May 21, 1987

[30] Foreign Application Priority Data

May 23, 1986 [DE] Fed. Rep. of Germany ....... 3617451

[51] Int. Cl.[4] .......................................... C07D 263/56
[52] U.S. Cl. .................... 548/106; 106/176; 524/94; 548/220; 548/224
[58] Field of Search .................. 548/106, 220, 224

[56] References Cited

U.S. PATENT DOCUMENTS 3,993,659 11/1976 Meyer .................................. 548/220
4,245,007 1/1981 Guglielmetti ...................... 548/224

FOREIGN PATENT DOCUMENTS 1195484 6/1970 United Kingdom ................ 548/220

Primary Examiner—Donald G. Daus
Assistant Examiner—Mark W. Noel

[57] ABSTRACT

Compounds of the general formula

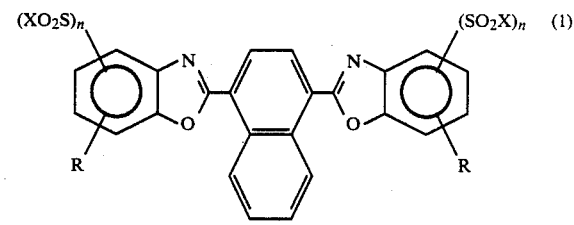

in which
n denotes 1 or 2,
X denotes an OMe group,
Me denotes a proton, an alkali metal cation or an optionally substituted ammonium cation,
R denotes hydrogen, a lower alkyl group or halogen, and, in the event that
n is 1,
X also denotes an $-NR^1R^2$ group in which $R^1$ and $R^2$ represent hydrogen or a lower alkyl group,
a process for their preparation and their use as optical brighteners, especially for polyamide fibers and wool.

3 Claims, No Drawings

BISBENZOXAZOLYLNAPHTHALENES CONTAINING SULFONATE OR SULFONAMIDE GROUPS, A PROCESS FOR THEIR PREPARATION AND THEIR USE

It is already known to use, as optical brighteners, bisbenzoxazolylnaphthalenes containing sulfonate groups and having a sulfonate group in the naphthalene nucleus. Thus, for example, dimethylammonium 1,4-bis-[benzoxazol-2-yl]-naphthalene-6-sulfonate is described as an optical brightener in German Offenlegungsschrift No. 2,645,301.

It has now been found that compounds of the general formula (1)

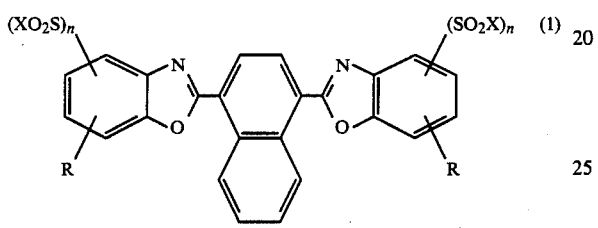

in which
n denotes 1 or 2,
X denotes an OMe group,
Me denotes a proton, an alkali metal cation or an optionally substituted ammonium cation,
R denotes hydrogen, a lower alkyl group or halogen and, in the event that
n is 1,
X also denotes an $-NR^1R^2$ group in which $R^1$ and $R^2$ represent hydrogen or a lower alkyl group,
are very good optical brighteners.

Preferred compounds of the formula (1) are those in which
n denotes 1,
X denotes an OMe or $NH_2$ group,
Me denotes a proton, an alkali metal cation or an optionally substituted ammonium cation and
R denotes hydrogen.

The compounds of the formula (2),

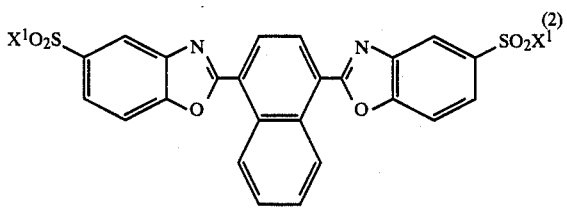

in which
$X^1$ denotes an OMe or $NH_2$ group and
Me denotes a proton, an alkali metal cation or an optionally substituted ammonium cation,
are of very particular interest.

In all cases lower alkyl groups contain 1 to 6, preferably 1 to 4, carbon atoms. Suitable optionally substituted ammonium cations are, above all, ammonium ions derived from a $C_1$-$C_4$-monalkylamine, -dialkylamine or -trialkylamine or a mono-, di- or tri-hydroxyethylamine or a mono-, di- or tri-hydroxypropyl-amine. Halogen preferably denotes chlorine or bromine.

The preparation of compounds of the formula (1) in which X denotes an OMe group can be effected in polyphosphoric acid by the condensation reaction expressed in the following equation, in which n and R have the meaning mentioned initially.

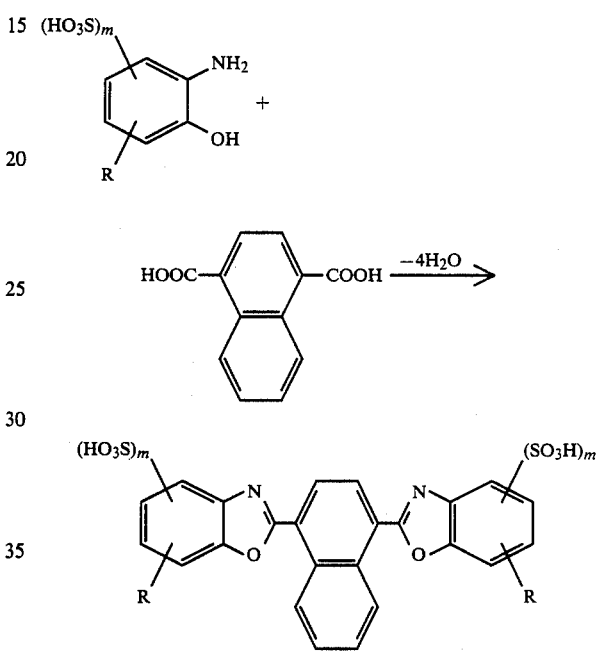

The brightener sulfonic acids thus obtained can be converted by neutralization into the corresponding salts embraced by the general formula (1). This condensation reaction is carried out at 120° to 200° C., preferably 140° to 180° C.

The sulfonamides of the general formula (1) can be prepared in accordance with the equation below by reacting the acid chloride of naphthalene-1,4-dicarboxylic acid with corresponding o-aminophenolsulfonamides and subsequent elimination of water.

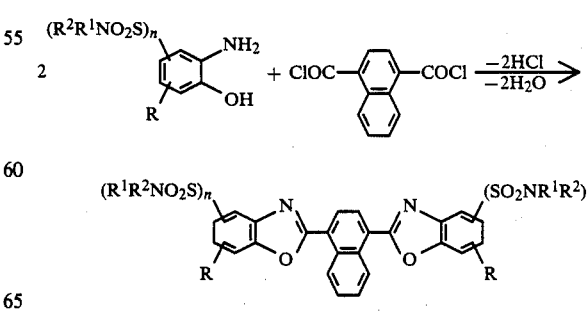

The above reaction can be carried out with or without isolating the acylamino compound

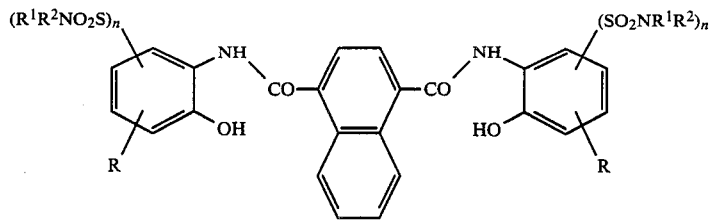

which is formed as an intermediate stage. Solvents which can be used for the acylation are aprotic solvents, such as dichlorobenzene, trichlorobenzene, methylbenzoate, tetralin, N-methylpyrrolidone and dimethylformamide. The elimination of water is preferably effected in the presence of acid catalysts, such as zinc chloride, p-toluenesulfonic acid, N-methylpyrrolidone hydrochloride or boric acid. The temperatures employed for the formation of the benzoxazole are 140° to 210° C. If suitable solvents are selected, the process above can also be employed to prepare the brightener disulfonic acids according to the invention.

The sulfonamides according to the invention can also be prepared by converting the brightener sulfonic acids into the corresponding sulfochlorides and then reacting the latter with amines of the formula $HNR^1R^2$. The customary reagents, such as thionyl chloride, phosphorus trichloride and phosphorus pentachloride, are suitable for the preparation of the sulfochlorides.

The following are examples of o-aminophenolsulfonic acids and o-aminophenolsulfonamides which can be employed:

2-aminophenol-4-sulfonic acid
2-aminophenol-5-sulfonic acid
4-methyl-2-aminophenol-6-sulfonic acid
6-methyl-2-aminophenol-4-sulfonic acid
4-chloro-2-aminophenol-6-sulfonic acid
6-chloro-2-aminophenol-4-sulfonic acid
2-aminophenol-4,6-disulfonic acid
2-aminophenol-4-sulfonamide
2-aminophenol-5-sulfonamide In a dissolved or finely divided state, the new compounds according to the invention display, to a varying degree, a pronounced fluorescence. They are used for optically brightening a very wide variety of synthetic, semi-synthetic or natural organic materials.

The following groups of organic materials may be mentioned as examples of these, without any limitation thereto being expressed by the following list:

1. Polymerization products, for example polymers based on $\alpha,\beta$-unsaturated carboxylic acids or derivatives of such carboxylic acids, in particular on acrylic compounds and olefin hydrocarbons, and polymers based on vinyl and vinylidene compounds.

2. Polymerization products which can be obtained by ring-opening, for example polyamides of the polycaprolactam type, and also polymers which can be obtained either via polyaddition or via polycondensation, such as polyethers or polyacetals.

3. Polycondensation products or precondensates based on difunctional or polyfunctional compounds containing groups capable of condensation, and homocondensation and cocondensation products thereof, such as, for example, polyesters, in particular saturated polyesters (for example ethylene glycol terephthalic acid polyesters), unbranched polyesters and branched polyesters (including those based on polyhydric alcohols, such as, for example, alkyd resins), and polyamides (for example hexamethylenediamine adipate).

4. Semi-synthetic organic materials, for example cellulose esters of varying degrees of esterification (secondary acetate and triacetate), cellulose ethers or regenerated cellulose.

5. Natural organic materials of animal or vegetable origin, for example those based on cellulose or proteins, such as cotton, wool, linen and silk.

Preferred organic materials are those composed of polyamide and wool.

The organic materials to be optically brightened can be in a very wide range of states of processing (raw materials, semifinished products or finished products).

Fiber materials can, for example, be in the form of continuous filaments (drawn or undrawn), staple fibers, flocks, hanks, textile threads, yarns, twists, nonwovens, felts, wadding or flocked structures or in the form of textile woven fabrics or textile composite materials or knitted fabrics and in the form of paper, cardboard or paper compositions.

The compounds to be used in accordance with the invention are, inter alia, of importance for the treatment of textile organic materials, in particular textile fabrics. If fibers, which can be in the form of staple fibers or continuous filaments or hanks, woven fabrics, knitted fabrics, nonwovens, flocked substrates or composite materials, are to be optically brightened in accordance with the invention, this is advantageously carried out in an aqueous medium in which the compounds concerned are present in a dissolved or finely divided form (suspensions or so-called microdispersions). If appropriate, dispersing agents, stabilizers, wetting agents and other auxiliaries can be added in the course of the treatment.

Depending on the type of brightener compound used, it can prove advantageous to carry out the treatment in a neutral or alkaline or acid liquor. The treatment is usually carried out at temperatures from about 20° to 140° C., for example at the boiling point of the bath or near to it (about 90° C.). Solutions or emulsions in organic solvents, in the manner practiced in the dyeing industry in so-called solvent dyeing (pad-mangel/heat-setting application and exhaust dyeing processes in dyeing machines), are also suitable for finishing textile substrates in accordance with the invention.

The new optical brighteners according to the present invention can also be added to or incorporated in the materials before they are shaped or while they are shaped. Thus they can, for example, be added to the compression molding material or injection molding material in the production of films, sheeting (for example incorporation into polyvinyl chloride by hot rolling) or moldings.

The new optical brighteners according to the present invention can, for example, also be employed in the following application forms:

1. Mixtures with dyestuffs (shading) or pigments or as an additive to dyebaths or print, discharge or resist pastes. Also for the after-treatment of dyeings, prints or discharge prints, 2. in mixtures with so-called carriers, wetting agents, softeners, swelling agents, antioxidants, light stabilizers, heat stabilizers and, particularly, chemical bleaching agents (chlorite bleaching or additives to bleaching baths), 3. mixed with crosslinking agents or finishing agents (for example starch or synthetic finishes) and in combination with a very wide variety of textile finishing processes, particularly the finishing of synthetic resins, and also the imparting of flameproofing, soft hand, soil-repellent or antistatic finishes or antimicrobial finishes, and 4. in combination with other substances having an optically brightening action.

In certain cases the full action of the brighteners is obtained by an after-treatment. This can be, for example, a chemical treatment (for example acid treatment), a thermal treatment (for example heat) or a combined chemical/thermal treatment. Thus, for example when optically brightening a number of fiber substrates, for example polyester fibers, by means of the brighteners according to the invention, a suitable procedure is to impregnate these fibers with aqueous dispersions (if appropriate also solutions) of the brighteners at temperatures below 75° C., for example at room temperature, and to subject them to a dry heat treatment at temperatures above 100° C., it being generally advisable additionally to dry the fiber material beforehand at a moderately elevated temperature, for example at at least 60° C. to about 130° C. The heat treatment in the dry state is then advantageously carried out at temperatures between 120° and 225° C., for example by heating in a drying oven, by ironing within the temperature range indicated or by treatment with dry, superheated steam.

The amount of the new optical brighteners to be used in accordance with the invention, relative to the material to be optically brightened, can vary within wide limits. A pronounced and permanent effect can be obtained even with very small amounts, in certain cases, for example, amounts of 0.0001% by weight. For most practical purposes, amounts between 0.01 and 0.5% by weight are of preferential interest.

The brighteners according to the invention can also be employed as a mixture with other brighteners. Since some of the brighteners according to the invention produce brightening effects having a green shade, it is particularly advantageous to use them together with brighteners which display reddish-tinged brightening effects.

The new optical brighteners have the particular advantage that they are also effective in the presence of donors of active chlorine, such as, for example, hypochlorite, and can be used without appreciable loss of the effects in washing baths containing nonionic detergents, for example alkylphenyl polyglycol ethers.

In the examples, unless otherwise specified, parts are always parts by weight and percentages are always percentages by weight. Unless a note is made to the contrary, melting points and boiling points are uncorrected.

Example 1

54.05 g of naphthalene-1,4-dicarboxylic acid, mixed with 99.35 g of 2-aminophenol-4-sulfonic acid (calculated on the basis of 100% strength) are introduced at 80° to 100° C. into 750 g of polyphosphoric acid, and the reaction mixture is heated to 150° to 160° C. and is stirred at this temperature for 4 hours. After cooling to 100° C., the reaction mixture is poured into 1500 ml of water and neutralized with concentrated sodium hydroxide solution (approx. 1800 g of 33% strength). The mixture is heated to the boil again for a short time and the product is filtered off with suction at room temperature and rinsed with 10% strength salt solution. Drying at 100° C. in vacuo gives 155 g of a pale yellow product containing salt, which can be purified further, for example by recrystallization from aqueous dimethylformamide. The resulting disodium salt of 1,4-bis-[5-sulfobenzoxazol-2-yl]-naphthalene (11) does not melt below 360° C.

Example 2

54.05 g of naphthalene-1,4-dicarboxylic acid are suspended in 300 ml of N-methylpyrrolidone, 52 g of thionyl chloride are added slowly at 10° to 15° C., and the mixture is stirred for a further hour at room temperature. 99.35 g of 2-aminophenol-4-sulfonic acid (calculated on the basis of 100% strength) are then introduced, and the mixture is heated to 150° C. in the course of approx. 1 to 2 hours and is stirred for approx. 3 hours more at this temperature. After cooling to 100° C., the reaction mixture is poured into 1200 ml of water and is rendered alkaline with concentrated sodium hydroxide solution, 150 g of sodium chloride are added and the mixture is heated at the boil for 30 minutes. After cooling to room temperature the product is filtered off with suction and rinsed with 10% strength salt solution. Drying at 100° C. gives approx. 110 g of a dark yellow product containing salt. The compound (11) is obtained in a pure form after being recrystallized from aqueous dimethylformamide or being dissolved in water and precipitated with acetone.

Example 3

54.05 g of naphthalene-1,4-dicarboxylic acid are suspended in 200 ml of toluene, to which 0.2 ml of pyridine is added. The mixture is heated to 70° C., 52 g of thionyl chloride are added, and the mixture is heated further to 110° C. in the course of 3 hours. A solution is formed. The solvent is then removed completely by distillation and the acid chloride which remains is taken up in 200 ml of anhydrous acetone. The resulting acetone solution is run into a suspension of 79 g of 2-aminophenol-4-sulfonamide in 200 ml of anhydrous acetone and 48 g of dimethylaniline, and the mixture is heated under reflux for 2 hours. After cooling, it is diluted with 400 ml of water, acidified with 23 g of concentrated hydrochloric acid and heated again under reflux for half an hour, and the product is filtered off when cold and is washed with water until neutral. Drying in vacuo at 100° C. gives the acylamino compound in a yield of 108.5 g, melting point 239°–240° C.

The acylamino compound obtained is heated at 210° C. under nitrogen for 3 hours in 500 ml of 1,2,4-trichlorobenzene to which 3 g of p-toluenesulfonic acid are added. After cooling to room temperature the product is filtered off with suction and rinsed with methanol. The moist material on the filter is thoroughly stirred again with dilute ammonium hydroxide solution and is isolated once more, washed with water until neutral and dried in vacuo at 100° C. 71.0 g of a yellow-brown product are obtained. Yellow 1,4-bis-[5-sulfamoylbenzoxazol-2-yl]-naphthalene (18) melts at 316° to 318° C. after recrystallization from ethylene glycol.

The compounds (12) to (17) shown in the following table can also be prepared analogously, as indicated in Examples 1 to 2.

TABLE

| Serial No. | A | Absorption[a] max [nm] · 10⁻⁴ | | Fluorescence[b] max [nm] | Q[b] |
|---|---|---|---|---|---|
| (11) | NaO₃S-(benzoxazol-2-yl) | 365 | 3.16 | 441 | 0.81 |
| (12) | (benzoxazol-2-yl) with NaO₃S at 6-position | 368 | 3.47 | 446 | 0.84 |
| (13) | CH₃-(benzoxazol-2-yl)-SO₃Na | 372 | 3.27 | 447 | 0.88 |
| (14) | Cl-(benzoxazol-2-yl)-SO₃Na | 374 | 3.22 | 447 | 0.82 |
| (15) | NaO₃S-(benzoxazol-2-yl)-CH₃ | 365 | 3.17 | 443 | 0.80 |
| (16) | NaO₃S-(benzoxazol-2-yl)-Cl | 364 | 2.89 | 443 | 0.76 |
| (17) | NaO₃S-(benzoxazol-2-yl)-SO₃Na | 373 | 2.93 | 444 | 0.86 |
| (18) | H₂NO₂S-(benzoxazol-2-yl) | 374[c] | 3.50 | 438[c] | 0.71 |

[a]Measured in 3:2 DMF/water
[b]Quantum yield
[c]Measured in DMF

USE EXAMPLES

Example 4

20 g of nylon-6 taffeta were brightened in a laboratory beam dyeing apparatus. The water-soluble compound from Example 1 of the formula

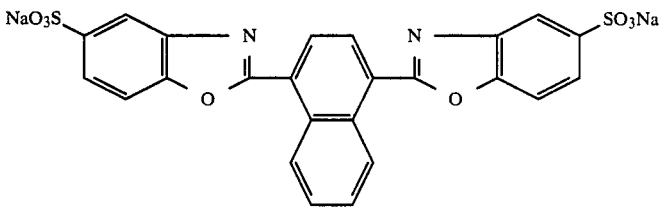

was used.
Liquor composition:
Liquor ratio 20:1,
0.25% of optical brightener (100% strength active substance, on weight of fiber),
2 g/l of Na acetate,
1 ml/l of 100% strength acetic acid and
0.5 g/l of nonylphenol polyglycol ether (nonylphenol-+approx. 8 EO).

The starting temperature was approx. 40° C.; the liquor was heated to 85° C. in the course of about 30 minutes and brightening was carried out at this temperature for a further 30 minutes. At the end of the cooling phase of the apparatus, the goods were vigorously rinsed under hot and cold conditions and were centrifuged. Drying was carried out at just under 100° C. A white of very good brilliance was obtained. Determination of reflectance on a DMC 25 reflectance spectrophotometer and calculating the whiteness value using the Ganz formula:

$$Wg = (D\ Y) + (P\ x) + (Q\ Y) + C$$

gave the excellent value of 254.

Example 5

Bleaching with Na chlorite and brightening using the compound according to Example 1 were carried out in a single bath in a laboratory beam dyeing apparatus.
Material: 20 g of nylon-6 taffeta. Liquor ratio: 20:1.
0.25% of optical brightener,
1.25 g/l of 100% strength Na chlorite,
1.2 g/l of Na nitrate,
1.2 g/l of potassium hydrogentartrate and
0.5 g/l of nonylphenol oxethylate (nonylphenol+approx. 8 EO).

The treatment, in particular the temperature control, was carried out as described under Example 4.

The result of this was a white which markedly surpassed the brightening obtained in Example 4. A whiteness value of 276 (Ganz formula) was found.

The compound according to Example 3 was employed for further examples.

[Chemical structure: bis-benzoxazole naphthalene compound with H₂NO₂S and SO₂NH₂ substituents]

The compound is not water-soluble; it was dispersed as follows:
0.100 g of substance were dissolved at the boil in 10 ml of a 1+1 mixture of DMF and nonylphenol oxethylate (nonylphenol+23 EO).

The boiling solution was introduced quantitatively, with vigorous stirring, into approx. 70 ml of water. 0.5 g of partly saponified polyvinyl alcohol had previously been dissolved in the water. After the resulting dispersion had cooled to room temperature while being stirred, it was made up to 100 ml.

Example 6

Laboratory beam dyeing apparatus, liquor ratio 20:1, demineralized water,
30 g of nylon-6 taffeta,
30.0 ml of the dispersion described (=0.15% of the compound according to Example 3 (100% strength) on weight of fiber),
3 g/l of Na acetate and
1 ml/l of 100% strength acetic acid in
400 ml of liquor.

The procedure was as in Example 1.

A whiteness value of 249 was achieved (Ganz formula).

Example 7

Na chlorite bleaching and brightening in a single bath in accordance with Example 5. Instead of the compound mentioned in that Example, a dispersion of the compound according to Example 3 was employed for brightening, as described above. Laboratory beam dyeing apparatus. 20 g of nylon taffeta, liquor ratio 20:1, demineralized water,
30.0 ml of brightener dispersion (=0.15% of the compound according to Example 3, on a 100% basis on weight of fiber),
1.25 g/l of Na chlorite,
1.2 g/l of Na nitrate,
1.2 g/l of anionic surfactant and
2.0 g/l of potassium hydrogentartrate.

The temperature control and the treatment were as indicated in Example 4.

This compound also afforded a better white in the presence of Na chlorite. The whiteness value was found to be 266 (Ganz formula). The whitness value of nylon-6 taffeta ((unbleached material) is 77 (Ganz formula).

We claim:

1. A compound of the formula (1),

[Chemical structure of formula (1): bis-benzoxazole naphthalene with (XO₂S)ₙ and (SO₂X)ₙ substituents and R groups]

in which
n denotes 1 or 2,
X denotes an OMe group,
Me denotes a proton, an alkali metal cation or an unsubstituted or mono-, di-, or tri-hydroxy-substituted (lower alkyl) ammonium cation,
R denotes hydrogen, a lower alkyl group or halogen, and, in the event that
n is 1,
X also denotes an —NR¹R² group in which R¹ and R² represent hydrogen or a lower alkyl group.

2. A compound of the formula (1) of claim 1 in which
n denotes 1,
X denotes an OMe or NH₂ group,
Me denotes a proton, an alkali metal cation or an unsubstituted or mono-, di- or tri-hydroxy-substituted (lower alkyl) ammonium cation and
R denotes hydrogen.

3. A compound of the formula (2)

[Chemical structure of formula (2): bis-benzoxazole naphthalene with XO₂S and SO₂X substituents]

in which
X denotes an OMe or NH₂ group and
Me denotes a proton, an alkali metal cation or an unsubstituted or mono-, di-, or tri-hydroxy-substituted (lower alkyl) ammonium cation.

* * * * *